United States Patent [19]
Firestone

[11] Patent Number: 5,990,110
[45] Date of Patent: Nov. 23, 1999

[54] METHOD FOR TREATING TUMORS HAVING HIGH LDL REQUIREMENTS EMPLOYING MTP INHIBITORS

[75] Inventor: Raymond A. Firestone, New Haven, Conn.

[73] Assignee: Bristol-Meyers Squibb Company, Princeton, N.J.

[21] Appl. No.: 08/914,062

[22] Filed: Jul. 15, 1997

[51] Int. Cl.$^6$ .................. A61K 31/495; A61K 31/445
[52] U.S. Cl. .................. 514/252; 514/326; 514/329
[58] Field of Search .................. 514/252, 326, 514/329

[56] References Cited

U.S. PATENT DOCUMENTS 5,712,279  1/1998  Biller et al. .................. 514/252

OTHER PUBLICATIONS

Firestone, R.A. "Low–Density Lipoprotein as a Vehicle for Targeting Antitumor Compounds to Cancer Cells" Bioconjugate Chem., vol. 5, No. 2, 1994, pp. 105–113.

Wunderlich, M. et al, "The Redox Properties of Protein Disulfide Isomerase (DsbA) of *Escherichia coli* Result from a Tense Conformation of its Oxidized Form", J. Mol. Biol. (1993) 233, 559–566.

Firestone, R.A. et al, "Selective Delivery of Cytotoxic Compounds to Cells by the LDL Pathway" Journal of Medicinal Chem., 1984, vol. 27, No. 8, pp. 1037–1043.

*Primary Examiner*—Raymond Henley, III
*Attorney, Agent, or Firm*—Burton Rodney

[57] ABSTRACT

A method is provided for treating hematologic tumors and solid tumors, including certain types of leukemias and metastatic tumors, having high LDL requirements employing a delipidating agent such as an MTP inhibitor to substantially reduce LDL blood levels. In addition, a method is provided for treating tumors of the above types having high LDL requirements, especially hematologic tumors such as certain leukemias, employing a delipidating compound to substantially remove native LDL, and then administering a cytotoxic agent carried in reconstituted LDL.

29 Claims, No Drawings

METHOD FOR TREATING TUMORS HAVING HIGH LDL REQUIREMENTS EMPLOYING MTP INHIBITORS

FIELD OF THE INVENTION

The present invention relates to a method for treating cancers having high LDL requirements employing a delipidating agent, which preferably is an MTP inhibitor, alone or in combination with a cytotoxic agent.

BACKGROUND OF THE INVENTION

It is known that cancer cells need cholesterol to make new cell membrane. The cholesterol is supplied by either de novo synthesis or from low-density lipoprotein (LDL), or both, Firestone, R. A. et al, "Selective Delivery of Cytotoxic Compounds to Cells by the LDL Pathway, J. Med. Chem., 1984, 27, 1037–1043. Firestone et al describe a series of cytotoxic compounds that are compatible with reconstituted LDL and may be delivered with reconstituted LDL against cancers that copiously internalize LDL.

Firestone, R. A., "Low-Density Lipoprotein as a Vehicle for Targeting Antitumor Compounds to Cancer Cells", Bioconjugate Chemistry, 1994, 5, pp 105–113, at page 105, in the "Introduction", discusses problems associated with cancer treatment as follows:

"It is difficult to eradicate cancer cells in vivo because they share with normal cells, for the most part, the same biochemical machinery. There is no cytotoxic substance that is completely selective for malignant cells, and all those presently in use cause dose-limiting toxic side effects. For this reason there is a growing emphasis on targeting, i.e., selective delivery of drugs to tumors in ways that bypass normal body tissues.

"Among the vehicles that can be used for this purpose is low-density lipoprotein (LDL), a normal blood constituent that is the body's principal means for delivery of cholesterol to tissues. Cholesterol, a major constituent of mammalian cell membranes, is obtained by cells either by making it themselves or by picking it up from LDL or both. Cancer cells, like all dividing ones, need large amounts of cholesterol because they are making new membrane. There is ample evidence that many types of cancer cells indeed have unusually great LDL requirements. The evidence is 2-fold: measurements of LDL uptake by tumor cells and depletion of LDL in the blood of cancer patients resulting from high uptake by the tumor (viae infra). Thus, if LDL could be made to carry antitumor drugs, it would serve as a targeting vehicle. This concept was proposed in 1981–2 (1,2) and has been reviewed several times since then (3–7)."

(1) Gal, D., Ohashi, J., MacDonald, P. C., Buchsbaum, H. J., and Simpson, E. R. (1981) Low-density lipoprotein as a potential vehicle for chemotherapeutic agents and radionucleotides in the management of gynecologic neoplasms. *Am. J. Obstet. Gynecol.* 139, 877.

(2) Counsell, R. E., and Pohland, R. C. (1982) Lipoproteins as potential site-specific delivery systems for diagnostic and therapeutic agents. *J. Med. Chem.* 25, 1115.

(3) van Berkel, T. J. C. (1993) Drug targeting: application of endogenous carriers for site-specific delivery of drugs. *J. Controlled Release* 24, 145.

(4) Vitols, S. (1991) Uptake of low-density lipoprotein by malignant cell—possible therapeutic applications. *Cancer Cells* 3, 488.

(5) deSmidt, P. C., and Van Berkel, T. J. C. (1990) LDL-mediated drug targeting. *Crit. Revs. Thera. Drug Carrier Syst.* 7, 99.

(6) Peterson, C., Masquelier, M., Rudling, M., Söderberg, K., and Vitols, S. (1991) Lipoproteins, malignancy and anticancer agents. *Targeted Diagn. Ther. (U.S.)* 5, 175.

(7) Catapano, A. L. (1987) Transport of cytotoxic compounds to cells via the LDL receptor pathway. *Med. Sci. Res.* 15, 411.

At page 105 under the topic "LDL Uptake . . .", Firestone, supra, lists numerous tumor types that have especially high LDL requirements including acute myeloid leukemia (AML), human monocytic (FAB-M5) and myelomonocytic (FAB-M4) leukemias, chronic myeloid leukemia in blast crisis, solid tumors such as epidermoid cervical cancer EC-50, endometrial adenocarcinoma AC-258, gastric carcinoma and parotid adenoma, G2 heptoma, squamous lung cancer, choriocarcinoma, brain tumors such as medulloblastoma, oligodendroglioma, glioma V-251MG, and malignant menigioma, as well as tumor cells that are exceptionally metastatic (Schroeder, F., Kier, A. B. Olson, C. D., and Dempsey, N. E. (1984) Correlation of tumor metastasis with sterol carrier protein and plasma membrane sterol levels. *Biochem. Biophys. Res. Commun.* 124, 283, and Cambien, F., Ducimetiere, P., and Richard, J. (1980) Total serum cholesterol and cancer mortality in a middle-aged male population. *Am. J. Epidemiol.* 112, 388), tumor cells that are exceptionally aggressive (Rudling, M. J., Stahle, L., Peterson, C. O., and Skoog, L. (1986) Content of low density lipoprotein receptors in breast cancer tissue related to survival of patients. *Brit. Med. J.* 292, 580;

Peterson, C., Vitols, S., Rudling, M., Blomgren, H., Edsmyr, F., and Skoog, L. (1985) Hypocholesterolemia in cancer patinets may be caused by elevated LDL receptor activities in malignant cells. *Med. Oncol. Tumor Pharmacother.* 2, 143;

Muller, C. P., Wagner, A. U., Maucher, C., and Steinke, B. (1989) Hypocholesterolemia, an unfavorable feature of prognostic value in chronic myeloid leukemia. *Eur. J. Hematol.* 43, 235), and tumor cells that are exceptionally undifferentiated (Ponec, M., Havekes, L., Kempenaar, J., Lavrijsen, S., Wijsman, M., Boonstra, J., and Vermeer, B. J. (1985) Calcium-mediated regulation of the low density lipoprotein receptor and intracellular cholesterol synthesis in human epidermal keratinocytes. *J. Cell Physiol.* 125 98;

Zyada, L. E., Hassan, H. T., Rees, J. K. H., and Ragab, M. H. (1990) The relation between hypocholesterolemia and degree of maturation in acute myeloid leukemia. *Hematol. Oncol.* 8, 65;

Ponec, M., Havekes, L., Kempenaar, J., Lavrisen, S., and Vermeer, B. J. (1984) Defective low-density lipoprotein metabolism in cultured, normal transformed and malignant keratinocytes. *J. Invest. Dermatol.* 83, 436).

Firestone, supra, on page 107 under the topic "Reconstitution of LDL With Cytotoxic Drugs" states as follows, "In order to kill tumors with drugs that are targeted in LDL, the drugs must somehow be bound to the LDL in such a way that (1) they cannot escape from it while traveling in the blood enroute to the tumor, (2) their cytotoxicity is chemically or physically masked while LDL-bound, and then restored after entering the target cells, (3) in quantity X killing power there is enough drug to kill cancer cells contained in the reconstituted LDL (r-LDL), whose uptake is limited by the number of LDL receptors on the tumor cells and their rate of internalization, and (4) the presence of Apo B and its binding power to LDL receptors are retained. The ability of the drug, once released from its carrier, to escape from lysosomes must also be taken in account (76)."

((76) Burton, R., et al (1975) The permeability properties of rat liver lysosomes to nucleotides. *Biochem. Soc. Trans.* 3, 1251).

On page 109, under the topic "Removal of LDL From the Patient Before Treatment", Firestone, supra, states as follows, "During treatment, drug-bearing r-LDL must compete with native LDL for access to LDL receptors on the tumor cells, requiring elevated doses of r-LDL. This can be countered by removing LDL from the patients' blood (delipidation) prior to treatment (139–141). Although restoration of normal LDL levels takes days (141), it might be best to delipidate immediately prior to treatment because it induces upregulation of LDL receptors throughout the body (142), and it is unknown whether upregulation in this way would be greater for tumor or normal cells."

((139) Franceschini, G., Busnach, G., Calabresi, L., Chiesa, G., Gianfranceschi, G., Zoppi, F., Minetti, L., and Sirtori, C. R. (1991) Predictability of low-density lipoprotein levels during apheretic treatment of hypercholesterolemia. *Eur. J. Clin. Invest.* 21, 209.

(140) Saal, S. D., Parker, T. S., Gordon, B. R., Studebaker, J., Hudgins, L., Ahrens, E. H., Jr., and Rubin, A. L. (1986) Removal of low-density lipoproteins in patients by extracorporeal immunoadsorption. *Am. J. Med.* 80, 583.

(141) Parker, T. S., Gordon, B. R., Saal, S. D., Rubin, A. L., and Ahrens, E. H., Jr. (1986) Plasma high density lipoprotein is increased in man when low density lipoprotein (LDL) is lowered by LDL-pheresis. *Proc. Nat. Acad. Sci. U.S.A.* 83, 777.

(142) Goldstein, J. L., and Brown M. S. (1977) The low-density lipoprotein pathway and its relation to atherosclerosis. *Annu. Rev. Biochem.* 46, 897).

The microsomal triglyceride transfer protein (MTP) catalyzes the transport of triglyceride (TG), cholesteryl ester (CE), and phosphatidylcholine (PC) between small unilamellar vesicles (SUV). Wetterau & Zilversmit, *Chem. Phys. Lipids* 38, 205–22 (1985). When transfer rates are expressed as the percent of the donor lipid transferred per time, MTP expresses a distinct preference for neutral lipid transport (TG and CE), relative to phospholipid transport. The protein from bovine liver has been isolated and characterized. Wetterau & Zilversmit, *Chem. Phys. Lipids* 38, 205–22 (1985). Polyacrylamide gel electrophoresis (PAGE) analysis of the purified protein suggests that the transfer protein is a complex of two subunits of apparent molecular weights 58,000 and 88,000, since a single band was present when purified MTP was electrophoresed under nondenaturing condition, while two bands of apparent molecular weights 58,000 and 88,000 were identified when electrophoresis was performed in the presence of sodium dodecyl sulfate (SDS). These two polypeptides are hereinafter referred to as 58 kDa and 88 kDa, respectively, or the 58 kDa and the 88 kDa component of MTP, respectively, or the low molecular weight subunit and the high molecular weight subunit of MTP, respectively.

Characterization of the 58,000 molecular weight component of bovine MTP indicates that it is the previously characterized multifunctional protein, protein disulfide isomerase (PDI). Wetterau et al.,*J. Biol. Chem.* 265, 9800–7 (1990). The presence of PDI in the transfer protein is supported by evidence showing that (1) the amino terminal 25 amino acids of the bovine 58,000 kDa component of MTP is identical to that of bovine PDI, and (2) disulfide isomerase activity was expressed by bovine MTP following the dissociation of the 58 kDa–88 kDa protein complex. In addition, antibodies raised against bovine PDI, a protein which by itself has no TG transfer activity, were able to immunoprecipitate bovine TG transfer activity from a solution containing purified bovine TP.

PDI normally plays a role in the folding and assembly of newly synthesized disulfide bonded proteins within the lumen of the endoplasmic reticulum. Bulleid & Freedman, *Nature* 335, 649–51 (1988). It catalyzes the proper pairing of cysteine residues into disulfide bonds, thus catalyzing the proper folding of disulfide bonded proteins. In addition, PDI has been reported to be identical to the beta subunit of human prolyl 4-hydroxylase. Koivu et al., *J. Biol. Chem.* 262, 6447–9 (1987). The role of PDI in the bovine transfer protein is not clear. It does appear to be an essential component of the transfer protein as dissociation of PDI from the 88 kDa component of bovine MTP by either low concentrations of a denaturant (guanidine HCl), a chaotropic agent (sodium perchlorate), or a nondenaturing detergent (octyl glucoside) results in a loss of transfer activity. Wetterau et al., *Biochemistry* 30, 9728–35 (1991). Isolated bovine PDI has no apparent lipid transfer activity, suggesting that either the 88 kDa polypeptide is the transfer protein or that it confers transfer activity to the protein complex.

The tissue and subcellular distribution of MTP activity in rats has been investigated. Wetterau & Zilversmit, *Biochem. Biophys. Acta* 875, 610–7 (1986). Lipid transfer activity was found in liver and intestine. Little or no transfer activity was found in plasma, brain, heart, or kidney. Within the liver, MTP was a soluble protein located within the lumen of the microsomal fraction. Approximately equal concentrations were found in the smooth and rough microsomes.

Abetalipoproteinemia is an autosomal recessive disease characterized by a virtual absence of plasma lipoproteins which contain apolipoprotein B (apoB). Kane & Havel in *The Metabolic Basis of Inherited Disease*, Sixth edition, 1139–64 (1989). Plasma TG levels may be as low as a few mg/dL, and they fail to rise after fat ingestion. Plasma cholesterol levels are often only 20–45 mg/dL. These abnormalities are the result of a genetic defect in the assembly and/or secretion of very low density lipoproteins (VLDL) in the liver and chylomicrons in the intestine. The molecular basis for this defect has not been previously determined. In subjects examined, triglyceride, phospholipid, and cholesterol synthesis appear normal. At autopsy, subjects are free of atherosclerosis. Schaefer et al., *Clin. Chem.* 34, B9–12 (1988). A link between the apoB gene and abetalipoproteinemia has been excluded in several families. Talmud et al., *J. Clin. Invest.* 82, 1803–6 (1988) and Huang et al.,*Am. J. Hum. Genet.* 46, 1141–8 (1990).

Subjects with abetalipoproteinemia are afflicted with numerous maladies. Kane & Havel, supra. Subjects have fat malabsorption and TG accumulation in their enterocytes and hepatocytes. Due to the absence of TG-rich plasma lipoproteins, there is a defect in the transport of fat-soluble vitamins such as vitamin E. This results in acanthocytosis of erythrocytes, spinocerebellar ataxia with degeneration of the fasciculus cuneatus and gracilis, peripheral neuropathy, degenerative pigmentary retinopathy, and ceroid myopathy. Treatment of abetalipoproteinemic subjects includes dietary restriction of fat intake and dietary supplementation with vitamins A, E and K.

In vitro, MTP catalyzes the transport of lipid molecules between phospholipid membranes. Presumably, it plays a similar role in vivo, and thus plays some role in lipid metabolism. The subcellular (lumen of the microsomal fraction) and tissue distribution (liver and intestine) of MTP have led to speculation that it plays a role in the assembly of plasma lipoproteins, as these are the sites of plasma lipoprotein assembly. Wetterau & Zilversmit, *Biochem. Biophys. Acta* 875, 610–7 (1986). The ability of MTP to catalyze the transport of TG between membranes is consistent with this hypothesis, and suggests that MTP may catalyze the transport of TG from its site of synthesis in the endoplasmic reticulum (ER) membrane to nascent lipoprotein particles within the lumen of the ER.

Olofsson and colleagues have studied lipoprotein assembly in HepG2 cells. Bostrom et al., *J. Biol. Chem.* 263, 4434–42 (1988). Their results suggest small precursor lipoproteins become larger with time. This would be consistent with the addition or transfer of lipid molecules to nascent lipoproteins as they are assembled. MTP may play a role in this process. In support of this hypothesis, Howell and Palade, *J. Cell Biol.* 92, 833–45 (1982), isolated nascent lipoproteins from the hepatic Golgi fraction of rat liver. There was a spectrum of sizes of particles present with varying lipid and protein compositions. Particles of high density lipoprotein (HDL) density, yet containing apoB, were found. iggins and Hutson, *J. Lipid Res.* 25, 1295–1305 (1984), reported lipoproteins isolated from Golgi were consistently larger than those from the endoplasmic reticulum, again suggesting the assembly of lipoproteins is a progressive event. However, there is no direct evidence in the prior art demonstrating that MTP plays a role in lipid metabolism or the assembly of plasma lipoprotein.

Recent reports (Science, Vol. 258, page 999, 1992; D. Sharp et al, Nature, Vol. 365, page 65, 1993) demonstrate that the defect causing abetalipoproteinemia is in the MTP gene, and as a result, the MTP protein. Individuals with abetalipoproteinemia have no MTP activity, as a result of mutations in the MTP gene, some of which have been characterized. These results indicate that MTP is required for the synthesis of apoB containing lipoproteins, such as VLDL, the precursor to LDL. It therefore follows that inhibitors of MTP would inhibit the synthesis of VLDL and LDL, thereby lowering VLDL levels, LDL levels, cholesterol levels, and triglyceride levels in animals and man.

Canadian Patent Application No. 2,091,102 published Mar. 2, 1994 (corresponding to U.S. application Ser. No. 117,362, filed Sep. 3, 1993 (file DC21b)) which is incorporated herein by reference), reports MTP inhibitors which also block the ipoproteins in a human hepatic cell line (HepG2 cells). This provides further support for the proposal that an MTP inhibitor would lower apoB containing lipoprotein and lipid levels in vivo. This Canadian patent application discloses a method for identifying the MTP inhibitors

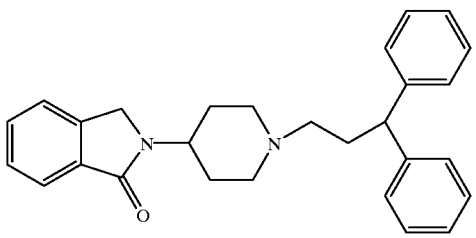

which has the name 2-[1-(3,3-diphenylpropyl)-4-piperidinyl]-2,3-dihydro-3-oxo-1H-isoindole hydrochloride and

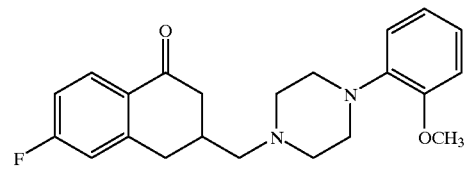

which has the name 1-[3-(6-fluoro-1-tetralanyl)methyl]-4-O-methoxyphenyl piperazine.

DESCRIPTION OF THE INVENTION

In accordance with the present invention, a method is provided for treating tumors having high LDL requirements which method includes the step of administering to a mammalian species in need of treatment a therapeutically effective amount of a delipidating agent to substantially reduce LDL blood levels.

In the above method, the delipidating agent may be optionally administered in combination with a cytotoxic agent.

In addition, in accordance with the present invention, a method is provided for treating tumors having high LDL requirements, especially hematologic tumors, which method includes the steps of administering to a mammalian species in need of treatment a therapeutically effective amount of a delipidating agent to substantially remove LDL (that is, native LDL), and administering a cytotoxic agent carried in reconstituted LDL (rLDL-drug conjugate).

The delipidating compound to be employed in the methods of the invention may be an LDL lowering compound which lowers LDL down to less than 20% of normal (that is less than 20% of 150 mg/dl that is 30 mg/dl), preferably down to less than 10% of normal (that is less than 15 mg/dl) and most preferably to substantially zero LDL. Examples of delipidating agents which may be employed herein include MTP inhibitors, statins, fibrates and resins or combinations thereof, with MTP inhibitors being preferred.

The reconstituted LDL (employed as a carrier for the cytotoxic agent in the above method) may be prepared according to the procedures described in the review article Firestone, R. A., Low-Density Lipoprotein as a Vehicle for Targeting Antitumor Compounds to Cancer Cells, Bioconjugate Chemistry, 1994, 5, 105–113, such as disclosed in the following references cited by Firestone, supra:

(78) Krieger, M., Brown, M. S., Faust, J. R., and Goldstein, J. L. (1978) Replacement of endogenous cholesteryl esters of low density lipoprotein with exogenous cholesteryl linoleate, *J. Biol. Chem.* 253, 4093.

(79) Krieger, M., McPhaul, J. J., Goldstein, J. L., and Brown, M. S. (1979) Replacement of neutral lipids of low density lipoprotein with esters of long chain unsaturated fatty acids, *J. Biol. Chem.* 254, 3845.

(104) Lundberg, B. (1987) Preparation of drug-low density lipoprotein complexes for delivery of antitumoral drugs via the low density lipoprotein pathway, *Cancer Res.* 47, 4105, and Gene M. Dubowchik and Raymond A. Firestone, *Tet. Lett.* 35, 4523, 1994.

The cytotoxic agent may be incorporated in the reconstituted LDL to form an LDL-drug conjugate following the procedure described in the Firestone review article, supra, especially as described in cited reference (104) Lundberg, supra.

MTP inhibitors to be employed in the methods of the invention include MTP inhibitors disclosed in Canadian Patent Application No. 2,091,102 described hereinbefore (corresponding to U.S. application Ser. No. 117,362), U.S. application Ser. No. 472,067, filed Jun. 6, 1995 (file DC21e), U.S. application Ser. No. 548,811 (file DC21h), U.S. provisional application No. 60/017,224, (file HX79a*), U.S. provisional application No. 60/017,253, (file HX82*) and U.S. provisional application No. 60/017,254, (file HX84*).

All of the above U.S. applications are incorporated herein by reference.

The MTP inhibitors disclosed in U.S. application Ser. No. 472,067, filed Jun. 6, 1995 (file DC21e) are piperidine compounds of the structure

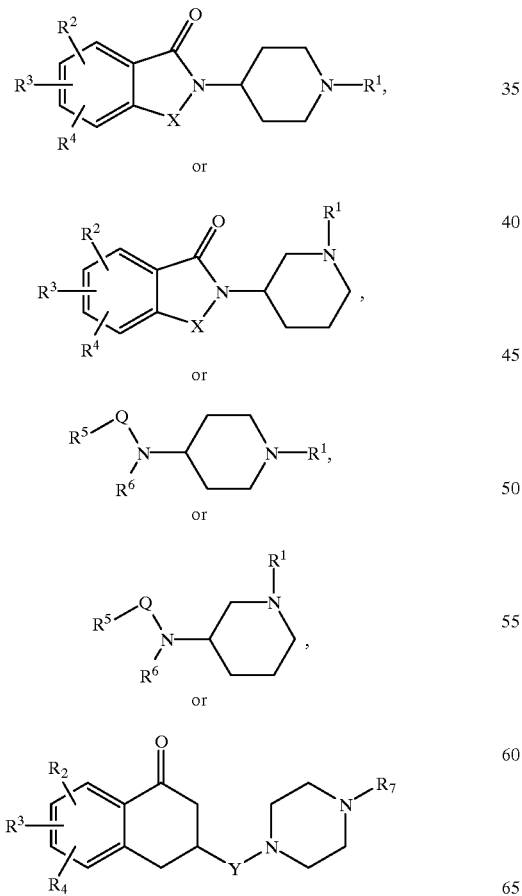

where Q is

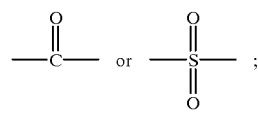

X is: $CHR^8$,

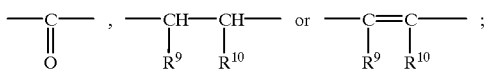

$R^8$, $R^9$ and $R^{10}$ are independently hydrogen, alkyl, alkenyl, alkynyl, aryl, arylalkyl, heteroaryl, heteroarylalkyl, cycloalkyl, or cycloalkylalkyl;

Y is $-(CH_2)_m-$ or

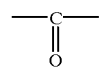

wherein m is 2 or 3;

$R^1$ is alkyl, alkenyl, alkynyl, aryl, heteroaryl, arylalkyl wherein alkyl has at least 2 carbons, diarylalkyl, arylalkenyl, diarylalkenyl, arylalkynyl, diarylalkynyl, diarylalkylaryl, heteroarylalkyl wherein alkyl has at least 2 carbons, cycloalkyl, or cycloalkylalkyl wherein alkyl has at least 2 carbons, all optionally substituted through available carbon atoms with 1, 2, 3 or 4 groups selected from halo, haloalkyl, alkyl, alkenyl, alkoxy, aryloxy, aryl, arylalkyl, alkylmercapto, arylmercapto, cycloalkyl, cyclo-alkylalkyl, heteroaryl, fluorenyl, heteroarylalkyl, hydroxy or oxo;

or $R^1$ is a fluorenyl-type group of the structure

A

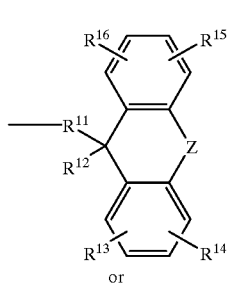

or

B

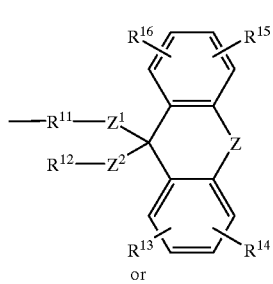

or

-continued

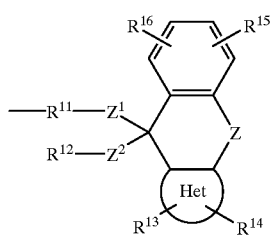

or

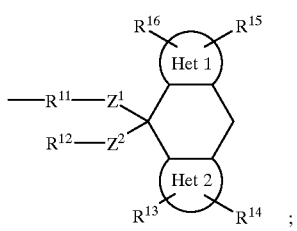

$R^1$ is an indenyl-type group of the structure

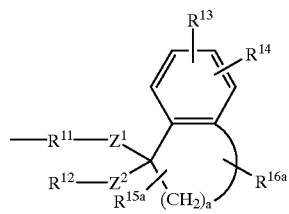

(a = 2, 3 or 4)

or

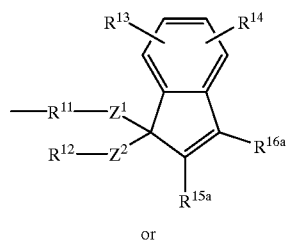

or

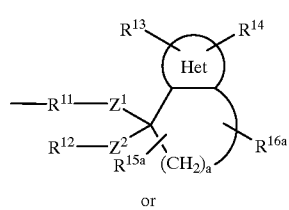

or

-continued

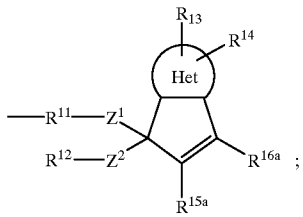

$Z^1$ and $Z^2$ are the same or different and are independently a bond, O, S,

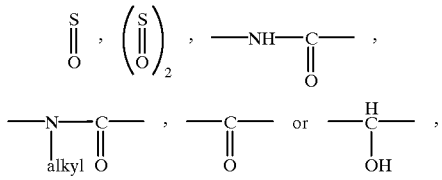

with the proviso that with respect to B, at least one of $Z^1$ and $Z^2$ will be other than a bond; $R^{11}$ is a bond, alkylene, alkenylene or alkynylene of up to 10 carbon atoms; arylene or mixed arylene-alkylene; $R^{12}$ is hydrogen, alkyl, alkenyl, aryl, haloalkyl, trihaloalkyl, trihaloalkylalkyl, heteroaryl, heteroarylalkyl, arylalkyl, arylalkenyl, cyclo-alkyl, aryloxy, alkoxy, arylalkoxy or cycloalkyl-alkyl, with the provisos that
(1) when $R^{12}$ is H, aryloxy, alkoxy or arylalkoxy, then $Z^2$ is

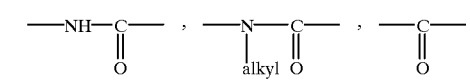

or a bond and
(2) when $Z^2$ is a bond, $R^{12}$ cannot be heteroaryl or heteroarylalkyl;

Z is bond, O, S, N-alkyl, N-aryl, or alkylene or alkenylene from 1 to 5 carbon atoms; $R^{13}$, $R^{14}$, $R^{15}$, and $R^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl or aryloxy;

$R^{15a}$ and $R^{16a}$ are independently hydrogen, alkyl, halo, haloalkyl, aryl, cycloalkyl, cycloheteroalkyl, alkenyl, alkynyl, alkoxy, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl, or aryloxy;

or $R^1$ is a group of the structure

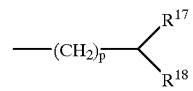

wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl at least one of $R^{17}$ and $R^{18}$ being other than H;

or $R^1$ is a group of the structure

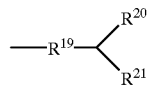

wherein $R^{19}$ is aryl or heteroaryl;

$R^{20}$ is aryl or heteroaryl;

$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;

$R^2$, $R^3$, $R^4$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;

$R^5$ is independently alkyl, alkenyl, alkynyl, aryl, alkoxy, aryloxy, arylalkoxy, heteroaryl, arylalkyl, heteroarylalkyl, cycloalkyl, cycloalkylalkyl, polycycloalkyl, polycycloalkylalkyl, cycloalkenyl, cycloheteroalkyl, heteroaryloxy, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino, thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, alkylsulfinyl;

$R^6$ is hydrogen or $C_1$–$C_4$ alkyl or $C_1$–$C_4$ alkenyl; all optionally substituted with 1, 2, 3 or 4 groups which may independently be any of the substituents listed in the definition of $R^5$ set out above;

$R^7$ is alkyl, aryl or arylalkyl wherein alkyl by itself or as part of arylalkyl is optionally substituted with oxo

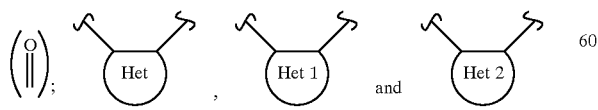

are the same or different and are independently selected from heteroaryl containing 5- or 6-ring members; and N-oxides

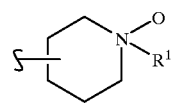

thereof; and pharmaceutically acceptable salts thereof;

with the provisos that where in the first formula X is $CH_2$, and $R^2$, $R^3$ and $R^4$ are each H, then $R^1$ will be other than 3,3-diphenylpropyl, and in the fifth formula, where one of $R^2$, $R^3$ and $R^4$ is 6-fluoro, and the others are H, $R^7$ will be other than 4-(2-methoxyphenyl).

The MTP inhibitors disclosed in U.S. application Ser. No. 548,811 filed Jan. 11, 1996 (file DC21h), have the structure

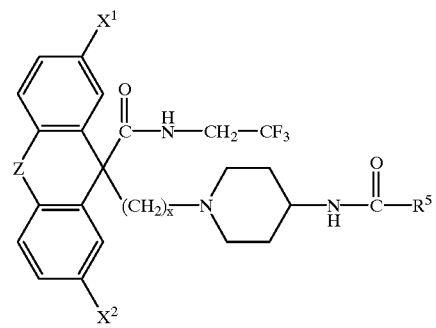

including the piperidine N-oxide thereof or a pharmaceutically acceptable salt thereof, wherein Z is a bond, O or S;

$X^1$ and $X^2$ are independently selected from H or halo;

x is an integer from 2 to 6;

$R^5$ is heteroaryl, aryl, heterocycloalkyl or cycloalkyl, each $R^5$ group being optionally substituted with 1, 2, 3 or 4 substituents which may be the same or different.

The MTP inhibitors disclosed in U.S. provisional application No. 60/017,224, filed May 9, 1996 (file HX79a*) have the structure

I

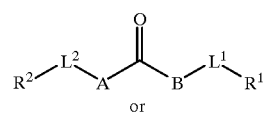

or

IA

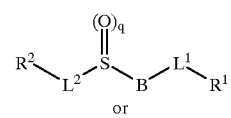

or

IB

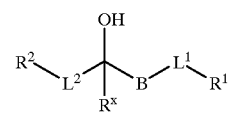

including pharmaceutically acceptable salts thereof, wherein q is 0, 1 or 2;

A is
(1) a bond;
(2) —O—; or

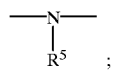  (3)

where $R^5$ is H or lower alkyl or $R^5$ together with $R^2$ forms a carbocyclic or heterocyclic ring system containing 4 to 8 members in the ring.

B is a fluorenyl-type group of the structure:

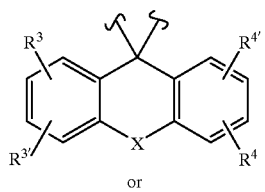

or

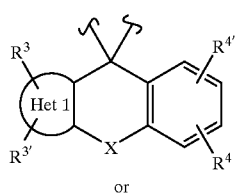

or

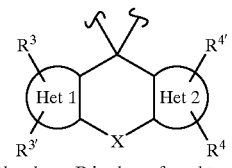

(the above B is also referred to as a fluorenyl-type ring or moiety); or

B is an indenyl-type group of the structure

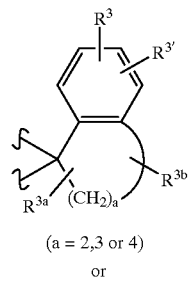

(a = 2, 3 or 4)

or

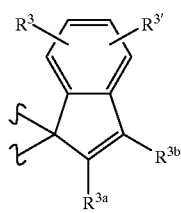

or

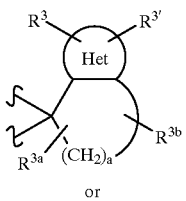

or

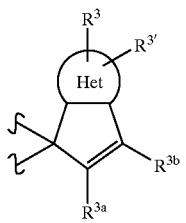

(the above B is also referred to as an indenyl-type ring or moiety);

$R^x$ is H, alkyl or aryl;

$R^1$ is alkyl, alkenyl, alkynyl, alkoxyl, (alkyl or aryl)$_3$Si (where each alkyl or aryl group is independent), cycloalkyl, cycloalkenyl, substituted alkylamino, substituted arylalkylamino, aryl, arylalkyl, arylamino, aryloxy, heteroaryl, heteroarylamino, heteroaryloxy, arylsulfonylamino, heteroarylsulfonylamino, arylthio, arylsulfinyl, arylsulfonyl, alkylthio, alkylsulfinyl, alkylsulfonyl, heteroarylthio, heteroarylsulfinyl, heteroarylsulfonyl, —PO($R^{13}$)($R^{14}$), (where $R^{13}$ and $R^{14}$ are independently alkyl, aryl, alkoxy, aryloxy, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy); $R^1$ can also be aminocarbonyl (where the amino may optionally be substituted with one or two aryl, alkyl or heteroaryl groups); cyano, 1,1-(alkoxyl or aryloxy)$_2$alkyl (where the two aryl or alkyl substituents can be independently defined, or linked to one another to form a ring, such as 1,3-dioxane or 1,3-dioxolane, connected to $L^1$ (or $L^2$ in the case of $R^2$) at the 2-position); 1,3-dioxane or 1,3-dioxolane connected to $L^1$ (or $L^2$ in the case of $R^2$) at the 4-position.

The $R^1$ group may have from one to four substituents, which can be any of the $R^3$ groups or $R^1$ groups, and any of the preferred $R^1$ substituents set out below.

$R^1$ may be substituted with the following preferred substituents: alkylcarbonylamino, cycloalkylcarbonylamino, arylcarbonylamino, heteroarylcarbonylamino, alkoxycarbonylamino, aryloxycarbonylamino, heteroaryloxylcarbonylamino, uriedo (where the uriedo nitrogens may be substituted with alkyl, aryl or heteroaryl), heterocyclylcarbonylamino (where the heterocycle is connected to the carbonyl group via a nitrogen or carbon atom), alkylsulfonylamino, arylsulfonylamino, heteroarylsulfonylamino,

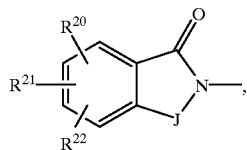

where J is: CHR²³,

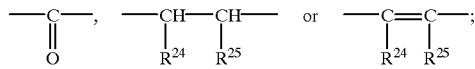

R²³, R²⁴ and R²⁵ are independently hydrogen, alkyl, alkenyl, alkynyl, aryl, arylalkyl, heteroaryl, heteroarylalkyl, cycloalkyl, or cycloalkylalkyl;

R²⁰, R²¹ R²² are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl; and these preferred substituents may either be directly attached to R¹, or attached via an alkylene chain at an open position.

R² is the same or different from R¹ and is independently any of the groups set out for R¹, H, polyhaloalkyl (such as CF₃CH₂, CF₃CF₂CH₂ or CF₃) or cycloheteroalkyl, and may be substituted with one to four of any of the groups defined for R³, or any of the substituents preferred for R¹.

L¹ is a linking group containing from 1 to 10 carbons in a linear chain (including alkylene, alkenylene or alkynylene), which may contain, within the linking chain any of the following: one or two alkenes, one or two alkynes, an oxygen, an amino group optionally substituted with alkyl or aryl, an oxo group; and may be substituted with one to five alkyl or halo groups (preferably F).

L² may be the same or different from L¹ and may independently be any of the L¹ groups set out above or a singe bond.

R³, R³', R⁴ and R⁴' may be the same or different and are independently selected from H, halogen, CF₃, haloalkyl, hydroxy, alkoxy, alkyl, aryl, alkenyl, alkenyloxy, alkynyl, alkynyloxy, alkanoyl, nitro, amino, thiol, alkylthio, alkylsulfinyl, alkylsulfonyl, carboxy, alkoxycarbonyl, aminocarbonyl, alkylcarbonyloxy, alkylcarbonylamino, cycloheteroalkyl, cycloheteroalkylalkyl, cyano, Ar, Ar-alkyl, ArO, Ar-amino, Ar-thio, Ar-sulfinyl, Ar-sulfonyl, Ar-carbonyl, Ar-carbonyloxy or Ar-carbonylamino, wherein Ar is aryl or heteroaryl and Ar may optionally include 1, 2 or 3 additional rings fused to Ar;

R³ᵃ and R³ᵇ are the same or different and are independently any of the R³ groups except hydroxy, nitro, amino or thio;

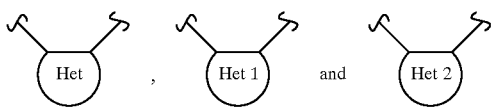

are the same or different and independently represent a 5 or 6 membered heteroaryl ring which may contain 1, 2, 3 or 4 heteroatoms in the ring which are independently N, S or O; and including N-oxides.

X (in the fluorenyl type ring) is a bond, or is one of the following groups:

(1)

(2)

(3)

(4)

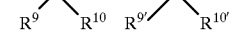

(5)

(6)

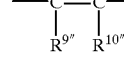

(7)

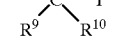

wherein

Y is O, N—R⁶ or S;

n' is 0, 1 or 2;

R⁶ is H, lower alkyl, aryl, —C(O)—R¹¹ or —C(O)—O—R¹¹;

R⁷ and R⁸ are the same or different and are independently H, alkyl, aryl, halogen, —O—R¹², or R⁷ and R⁸ together can be oxygen to form a ketone;

R⁹, R¹⁰, R⁹' and R¹⁰' are the same or different and are independently H, lower alkyl, aryl or —O—R¹¹;

R⁹'' and R¹⁰'' are the same or different and are independently H, lower alkyl, aryl, halogen or —O—R¹¹;

R¹¹ is alky or aryl;

R¹² is H, alkyl or aryl.

The following provisos apply to formula I compounds:

(a) when R¹ is unsubstituted alkyl or unsubstituted arylalkyl, L¹ cannot contain amino;

(b) when R¹ is alkyl, L¹ cannot contain amino and oxo in adjacent positions (to form an amido group);

(c) when R²L²A— is H₂N—, R¹L¹ cannot contain amino;

(d) when R¹ is cyano, L¹ must have more than 2 carbons;

(e) R¹L¹ must contain at least 3 carbons.

With respect to compounds IA and IB, R²L² cannot have an O or N atom directly attached to S=(O)_q or CR^x(OH), and for IA, R²L² cannot be H.

With respect to compounds IA and IB, where R¹ is cycloheteroalkyl, R¹ is exclusive of 1-piperidinyl, 1-pyrrolidinyl, 1-azetidinyl or 1-(2-oxopyrrolidinyl).

The MTP inhibitors disclosed in U.S. provisional application No. 60/017,253, filed May 10, 1996, (file HX82*) are pyrrolidine compounds and have the structure

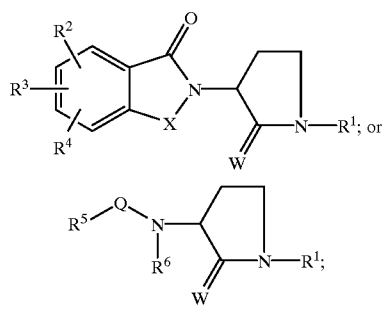

I

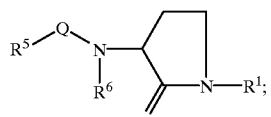

II where Q is

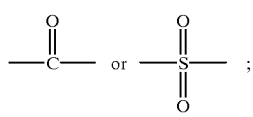

W is H,H or O; X is: CHR⁸,

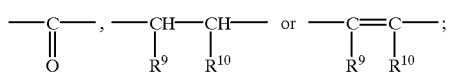

$R^8$, $R^9$ and $R^{10}$ are independently hydrogen, alkyl, alkenyl, alkynyl, aryl, arylalkyl, heteroaryl, heteroarylalkyl, cycloalkyl, or cycloalkylalkyl;

$R^1$ is alkyl, alkenyl, alkynyl, aryl, heteroaryl, arylalkyl (wherein alkyl preferably has at least 2 carbons, more preferably at least 3 carbons), diarylalkyl, arylalkenyl, diarylalkenyl, arylalkynyl, diarylalkynyl, diarylalkylaryl, heteroarylalkyl (wherein alkyl preferably has at least 2 carbons, more preferably at least 3 carbons), cycloalkyl, or cycloalkylalkyl (wherein alkyl preferably has at least 2 carbons, more preferably at least 3 carbons); all of the aforementioned $R^1$ groups being optionally substituted through available carbon atoms with 1, 2, 3 or 4 groups selected from halo, haloalkyl, alkyl, alkenyl, alkoxy, aryloxy, aryl, arylalkyl, alkyl-mercapto, arylmercapto, cycloalkyl, cycloalkyl-alkyl, heteroaryl, fluorenyl, heteroarylalkyl, hydroxy or oxo; or $R^1$ is a fluorenyl-type group of the structure

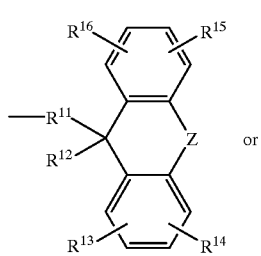

A

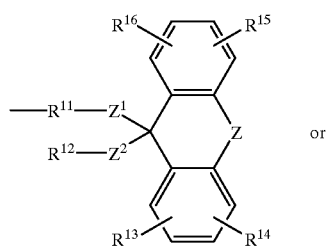

B

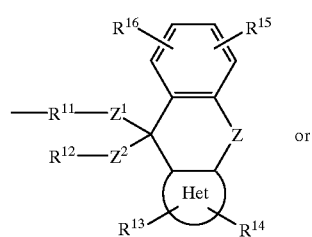

C

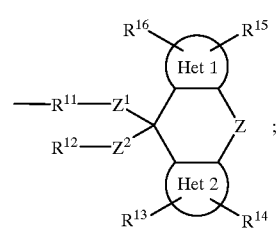

D or $R^1$ is an indenyl-type group of the structure

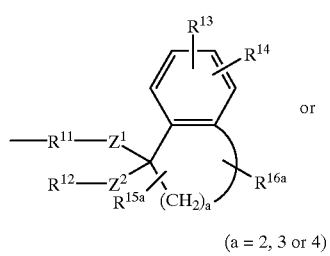

E (a = 2, 3 or 4)

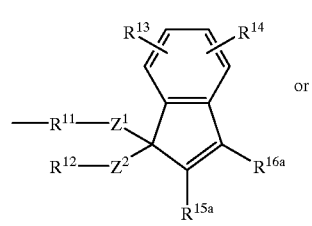

F

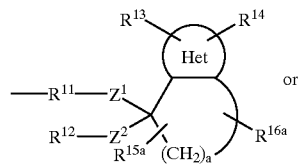

G

-continued

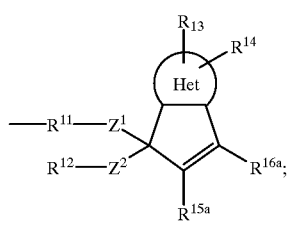

$Z^1$ and $Z^2$ are the same or different and are independently a bond, O, S,

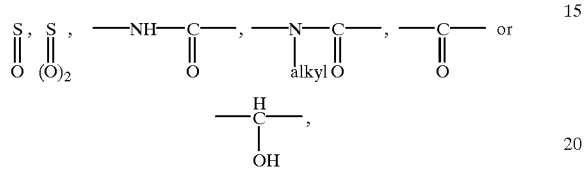

with the proviso that with respect to B, at least one of $Z^1$ and $Z^2$ will be other than a bond;

$R^{11}$ is a bond, alkylene, alkenylene or alkynylene of up to 10 carbon atoms, arylene (for example

), or mixed arylene-alkylene (for example

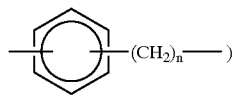)

where n is 1 to 6;

$R^{12}$ is hydrogen, alkyl, alkenyl, aryl, halo-alkyl, trihaloalkyl, trihaloalkylalkyl, heteroaryl, heteroarylalkyl, arylalkyl, arylalkenyl, cyclo-alkyl, aryloxy, alkoxy, arylalkoxy or cycloalkyl-alkyl; with the provisos that (1) when $R^{12}$ is H, aryloxy, alkoxy or arylalkoxy, then $Z^2$ is

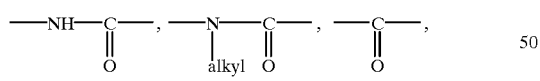

or a bond;
and (2) when $Z^2$ is a bond, $R^{12}$ cannot be heteroaryl or heteroarylalkyl;

Z is a bond, O, S, N-alkyl, N-aryl, or alkylene or alkenylene of from 1 to 5 carbon atoms;

$R^{13}$, $R^{14}$, $R^{15}$, and $R^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, aryl-sulfonyl, alkylthio, arylthio, aminocarbonyl, alkylcarbonyloxy, arylcarbonylamino, alkylcarbonyl-amino, arylalkyl, heteroaryl, heteroarylalkyl, or aryloxy;

$R^{15a}$ and $R^{16a}$ are independently any of the $R^{15}$ or $R^{16}$ groups except hydroxy, nitro, amino or thio;

or $R^1$ is

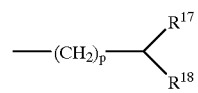

wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl, at least one of $R^{17}$ and $R^{18}$ being other than H;

or $R^1$ is

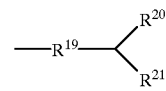

wherein $R^{19}$ is aryl or heteroaryl;

$R^{20}$ is aryl or heteroaryl;

$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;

$R^2$, $R^3$, $R^4$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;

$R^5$ is alkyl, alkenyl, alkynyl, aryl, alkoxy, aryloxy, arylalkoxy, heteroaryl, arylalkyl, heteroarylalkyl, cycloalkyl, cycloheteroalkyl, heteroaryloxy, cycloalkylalkyl, polycycloalkyl, polycycloalkylalkyl, cycloalkenyl, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all of the $R^5$ substituents and $R^6$ substituents (set out hereinafter) being optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino (wherein the amino includes 1 or 2 substituents which are alkyl, aryl or heteroaryl, or any of the other aryl compounds mentioned in the definitions), thiol, alkylthio, arylthio, heteroarylthio, arylthioalkyl, alkylcarbonyl, arylcarbonyl, arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, or alkylsulfinyl. Where $R^5$ is phenyl, aryl, heteroaryl or cycloalkyl; this group preferably includes an ortho hydrophobic substituent such as alkyl, haloalkyl (with up to 5 halo groups), alkoxy, haloalkoxy (with up to 5 halo groups), aryl, aryloxy or arylalkyl;

$R^6$ is hydrogen or $C_1$–$C_4$ alkyl or $C_1$–$C_4$ alkenyl;

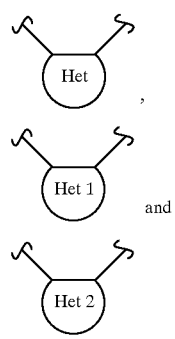

are the same or different and are independently selected from heteroaryl containing 5- or 6-ring members; and including N-oxides of the formulae I and II compounds, that is

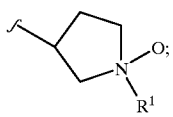

including pharmaceutically acceptable salts thereof.

The MTP inhibitors disclosed in U.S. provisional application No. 60/017,254, filed May 10, 1996, (file HX84*) are azetidine compounds which have the structure

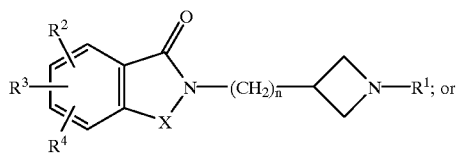

I

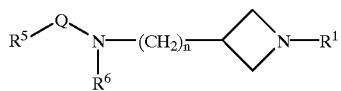

II where Q is

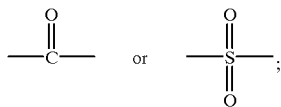

X is: $CHR^8$,

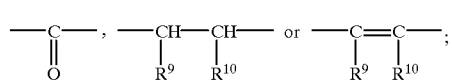

n is 0 or 1;

$R^8$, $R^9$ and $R^{10}$ are independently hydrogen, alkyl, alkenyl, alkynyl, aryl, arylalkyl, heteroaryl, heteroarylalkyl, cycloalkyl, or cycloalkylalkyl;

$R^1$ is alkyl, alkenyl, alkynyl, aryl, heteroaryl, arylalkyl (wherein alkyl preferably has at least 2 carbons, more preferably at least 3 carbons), diarylalkyl, arylalkenyl, diarylalkenyl, arylalkynyl, diarylalkynyl, diarylalkylaryl, heteroarylalkyl (wherein alkyl preferably has at least 2 carbons, more preferably at least 3 carbons), cycloalkyl, or cycloalkylalkyl (wherein alkyl preferably has at least 2 carbons, more preferably at least 3 carbons); all of the aforementioned $R^1$ groups being optionally substituted through available carbon atoms with 1, 2, 3 or 4 groups selected from halo, haloalkyl, alkyl, alkenyl, alkoxy, aryloxy, aryl, arylalkyl, alkylmercapto, arylmercapto, cycloalkyl, cycloalkylalkyl, heteroaryl, fluorenyl, heteroarylalkyl, hydroxy or oxo; or $R^1$ is a fluorenyl-type group of the structure

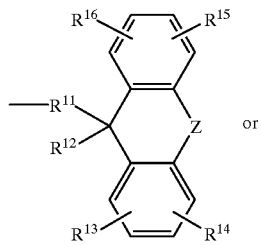

A

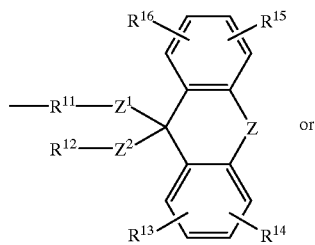

B

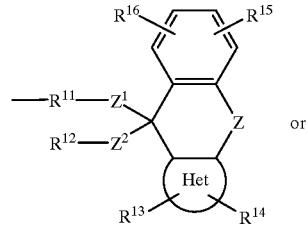

C

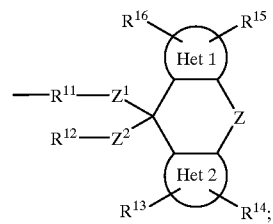

D or $R^1$ is an indenyl-type group of the structure

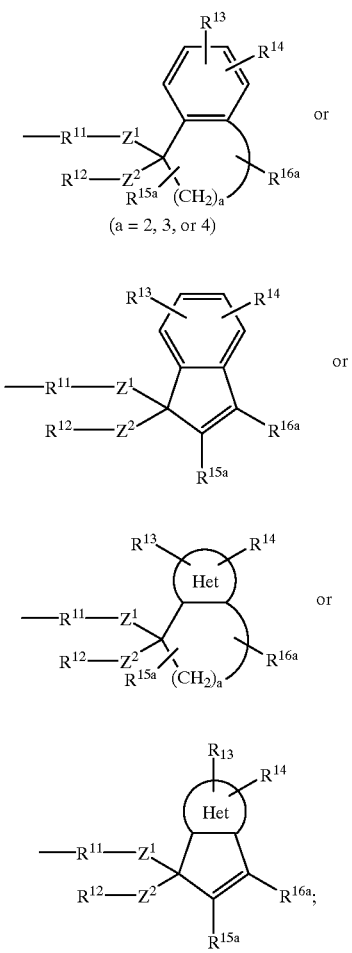

$Z^1$ and $Z^2$ are the same or different and are independently a bond, O, S,

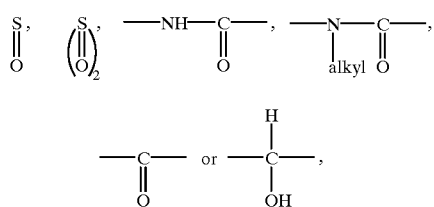

with the proviso that with respect to B, at least one of $Z^1$ and $Z^2$ will be other than a bond;

$R^{11}$ is a bond, alkylene, alkenylene or alkynylene of up to 10 carbon atoms, arylene (for example

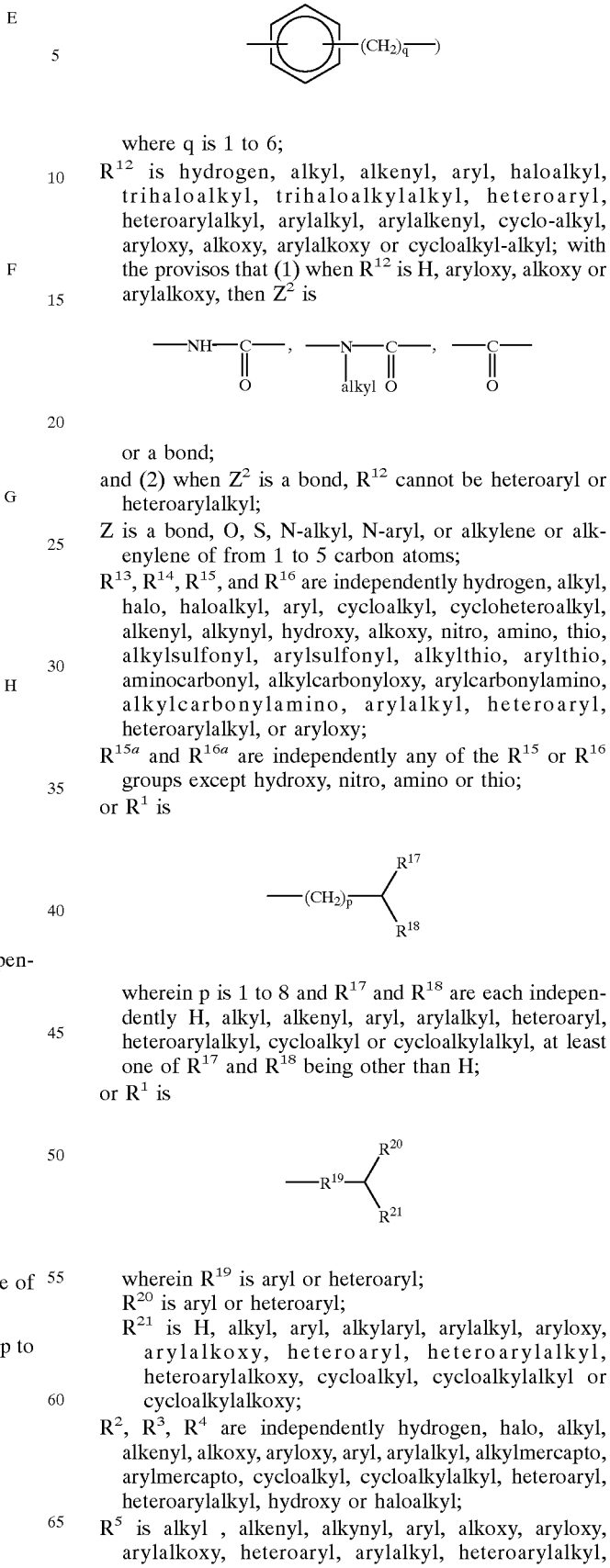

or mixed arylene-alkylene (for example where q is 1 to 6;
$R^{12}$ is hydrogen, alkyl, alkenyl, aryl, haloalkyl, trihaloalkyl, trihaloalkylalkyl, heteroaryl, heteroarylalkyl, arylalkyl, arylalkenyl, cyclo-alkyl, aryloxy, alkoxy, arylalkoxy or cycloalkyl-alkyl; with the provisos that (1) when $R^{12}$ is H, aryloxy, alkoxy or arylalkoxy, then $Z^2$ is or a bond;
and (2) when $Z^2$ is a bond, $R^{12}$ cannot be heteroaryl or heteroarylalkyl;
Z is a bond, O, S, N-alkyl, N-aryl, or alkylene or alkenylene of from 1 to 5 carbon atoms;
$R^{13}$, $R^{14}$, $R^{15}$, and $R^{16}$ are independently hydrogen, alkyl, halo, haloalkyl, aryl, cycloalkyl, cycloheteroalkyl, alkenyl, alkynyl, hydroxy, alkoxy, nitro, amino, thio, alkylsulfonyl, arylsulfonyl, alkylthio, arylthio, aminocarbonyl, alkylcarbonyloxy, arylcarbonylamino, alkylcarbonylamino, arylalkyl, heteroaryl, heteroarylalkyl, or aryloxy;
$R^{15a}$ and $R^{16a}$ are independently any of the $R^{15}$ or $R^{16}$ groups except hydroxy, nitro, amino or thio;
or $R^1$ is wherein p is 1 to 8 and $R^{17}$ and $R^{18}$ are each independently H, alkyl, alkenyl, aryl, arylalkyl, heteroaryl, heteroarylalkyl, cycloalkyl or cycloalkylalkyl, at least one of $R^{17}$ and $R^{18}$ being other than H;
or $R^1$ is wherein $R^{19}$ is aryl or heteroaryl;
$R^{20}$ is aryl or heteroaryl;
$R^{21}$ is H, alkyl, aryl, alkylaryl, arylalkyl, aryloxy, arylalkoxy, heteroaryl, heteroarylalkyl, heteroarylalkoxy, cycloalkyl, cycloalkylalkyl or cycloalkylalkoxy;
$R^2$, $R^3$, $R^4$ are independently hydrogen, halo, alkyl, alkenyl, alkoxy, aryloxy, aryl, arylalkyl, alkylmercapto, arylmercapto, cycloalkyl, cycloalkylalkyl, heteroaryl, heteroarylalkyl, hydroxy or haloalkyl;
$R^5$ is alkyl, alkenyl, alkynyl, aryl, alkoxy, aryloxy, arylalkoxy, heteroaryl, arylalkyl, heteroarylalkyl, cycloalkyl, cycloheteroalkyl, heteroaryloxy, cycloalkylalkyl, polycycloalkyl, polycycloalkylalkyl, cycloalkenyl, cycloalkenylalkyl, polycycloalkenyl, polycycloalkenylalkyl, heteroarylcarbonyl, amino, alkylamino, arylamino, heteroarylamino, cycloalkyloxy, cycloalkylamino, all of the $R^5$ substituents and $R^6$ substituents (set out hereinafter) being optionally substituted through available carbon atoms with 1, 2, 3 or 4 groups selected from hydrogen, halo, alkyl, haloalkyl, alkoxy, haloalkoxy, alkenyl, alkynyl, cycloalkyl, cycloalkylalkyl, cycloheteroalkyl, cycloheteroalkylalkyl, aryl, heteroaryl, arylalkyl, arylcycloalkyl, arylalkenyl, arylalkynyl, aryloxy, aryloxyalkyl, arylalkoxy, arylazo, heteroaryloxo, heteroarylalkyl, heteroarylalkenyl, heteroaryloxy, hydroxy, nitro, cyano, amino, substituted amino (wherein the amino includes 1 or 2 substituents which are alkyl, aryl or heteroaryl, or any of the other aryl compounds mentioned in the definitions), thiol, alkylthio, arylthio, heteroarylthio, arylthioalkyl, alkylcarbonyl, arylcarbonyl arylaminocarbonyl, alkoxycarbonyl, aminocarbonyl, alkynylaminocarbonyl, alkylaminocarbonyl, alkenylaminocarbonyl, alkylcarbonyloxy, arylcarbonyloxy, alkylcarbonylamino, arylcarbonylamino, arylsulfinyl, arylsulfinylalkyl, arylsulfonyl, alkylsulfonyl, arylsulfonylamino, heteroarylcarbonylamino, heteroarylsulfinyl, heteroarylthio, heteroarylsulfonyl, or alkylsulfinyl. Where $R^5$ is phenyl, aryl, heteroaryl or cycloalkyl; this group preferably includes an ortho hydrophobic substituent such as alkyl, haloalkyl (with up to 5 halo groups), alkoxy, haloalkoxy (with up to 5 halo groups), aryl, aryloxy or arylalkyl;

$R^6$ is hydrogen or $C_1$–$C_4$ alkyl or $C_1$–$C_4$ alkenyl;

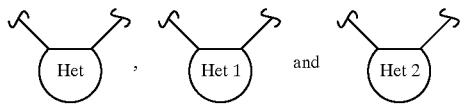

are the same or different and are independently selected from heteroaryl containing 5- or 6-ring members; and including N-oxides of the formulae I and II compounds, that is

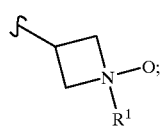

and including pharmaceutically acceptable salts thereof.

Compounds disclosed as preferred in each of the above applications are preferred for use in the present invention.

Most preferred MTP inhibitors to be employed in accordance with the present invention include preferred MTP inhibitors as set out in U.S. patent application Ser. No. 548,811, filed Jan. 11, 1996 (file DC21h) and in U.S. provisional application No. 60/017,224, filed May 9, 1996 (file HX79a*).

Thus, preferred compounds in U.S. patent application Ser. No. 548,811 (file DC21h) for use herein are compounds where Z is a bond;

$X^1$ and $X^2$ are H;

$R^5$ is aryl such as phenyl substituted with

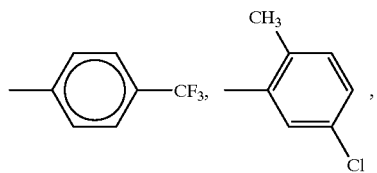

(1) aryl such as phenyl,

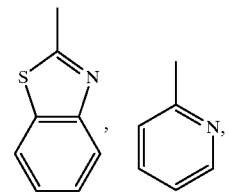

(2) heteroaryl such as (3) halo such as Cl $R^5$ is heteroaryl such as

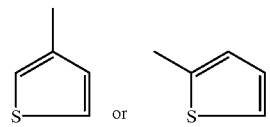

substituted with (1) aroyl such as

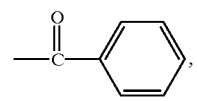

(2) arylthio such as

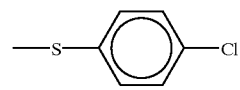

wherein the $R^5$ substituent is preferably in the position adjacent to the carbon linked to

$(CH_2)_x$ is —$(CH_2)_4$— or

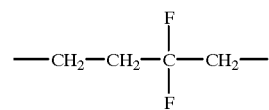

Most preferred is

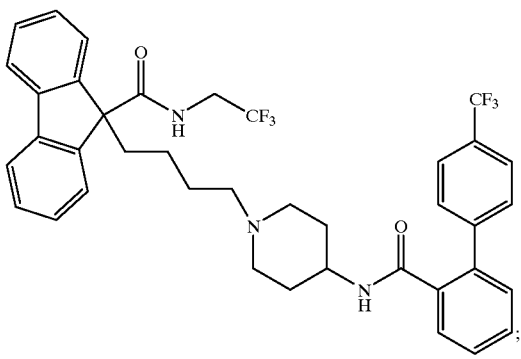

Preferred compounds in U.S. provisional application No. 60/017,224 (file HX79a*) for use herein are MTP inhibitor compounds of formula I that is

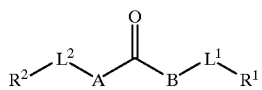

wherein

A is NH,

B is

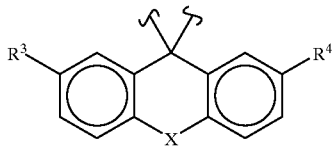

X is a bond, oxygen or sulfur; $R^3$ and $R^4$ are independently H or F.

Preferred $R^1$ groups are aryl, preferably phenyl, heteroaryl, preferably imidazoyl or pyridyl (preferably substituted with one of the preferred $R^1$ substituents: arylcarbonylamino, heteroarylcarbonylamino, cycloalkylcarbonylamino, alkoxycarbonylamino, alkylsulfonylamino, arylsulfonylamino, heteroarylsulfonylamino), $PO(OAlkyl)_2$, heteroarylthio, benzthiazole-2-thio, imidazole-2-thio, alkyl, or alkenyl, cycloalkyl such as cyclohexyl, or 1,3-dioxan-2-yl.

Preferred $R^2$ groups are alkyl, polyfluoroalkyl (such as 1,1,1-trifluoroethyl), alkenyl, aryl or heteroaryl (preferably substituted with one of the preferred $R^1$ substituents above), or $PO(OAlkyl)_2$.

If $R^2$ is alkyl, 1,1,1-trifluoroethyl, or alkenyl, it is preferred that $R^1$ is other than alkyl or alkenyl.

It is preferred that $L^1$ contains 1 to 5 atoms in the linear chain and $L^2$ is a bond or lower alkylene.

Preferred embodiments of formula IA and formula IB compounds of the invention include those where B, $L^1$, $L^2$, $R^1$ and $R^2$ are as set out with respect to the preferred embodiments of the formula I compounds, q is 0 or 2 and $R^x$ is H.

Examples of other delipidating agents which may be employed herein include statins such as pravastatin, lovastatin, simvastatin, atorvastatin, cerivastatin and fluvastatin, with pravastatin and atorvastatin being-preferred, fibrates such as clofibrate, fenofibrate, bezafibrate, gemfibrozil, ciprofibrate, and clinofibrate, as well as nicotinic acid, probucol and resins such as cholestyramine, colestipol, and DEAE-Sephadex, and/or combinations of two or more thereof, and/or combinations thereof with an MTP inhibitor.

The delipidating agent, for example MTP inhibitor employed in accordance with the present invention can be administered to various mammalian species, such as dogs, cats, humans, etc., in need of treatment. These agents can be administered systemically, such as orally or parenterally.

The delipidating agent, for example MTP inhibitor can be incorporated in a conventional systemic dosage form, such as a tablet, capsule, elixir or injectable formulation. The above dosage forms will also include the necessary physiologically acceptable carrier material, excipient, lubricant, buffer, antibacterial, bulking agent (such as mannitol), antioxidants (ascorbic acid or sodium bisulfite) or the like. Oral dosage forms are preferred, although parenteral forms are quite satisfactory as well.

The dose administered must be carefully adjusted according to the age, weight, and condition of the patient, as well as the route of administration, dosage form and regimen, and the desired result. In general, the dosage forms described above may be administered containing amounts of MTP inhibitor of from about 5 to about 500 mg per day preferably from about 10 to about 400 mg per day, in single or divided doses of one to four times daily.

The other delipidating agents will be employed in amounts set out in the latest edition of the Physician's Desk Reference (PDR).

Cytotoxic agents which may be employed in conjunction with the delipidating agent, for example with MTP inhibitors, in accordance with the present invention, are preferably lipophilic or rendered lipophilic by addition of LDL anchors such as oleoyl groups either as oleic acid derivatives or oleyl alcohol derivatives, linoleyl derivatives, retinyl derivatives or cholesteryl derivatives (as disclosed at page 107 of the Firestone review article, supra) so that the cytotoxic agent may be more easily constituted with LDL. Cytotoxic agents approved by the FDA such as those listed in the Physicians Desk Reference $50^{th}$ Ed. 1996, may be employed including doxorubicin, doxorubicin valerate, idarubicin HCl, mitomycin, paclitaxel, taxotere, teniposide, etoposide, carboplatin, busulfan, megestrol acetate, mitotane, altretamine, lomustine, carmustine, estramustine phosphate sodium, procarbazine hydrochloride, cytarabine, and the like.

Preferred cytotoxic agents include 9-methoxyellipticine, N-methylellipticinium, compounds 25, 1 and 2 disclosed in Firestone review article, supra, at page 107, that is

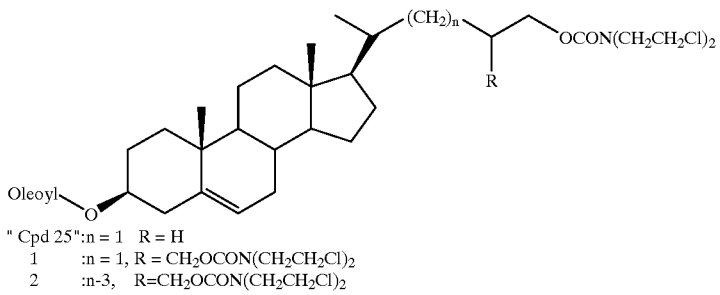

"Cpd 25": n = 1  R = H
1    : n = 1, R = CH₂OCON(CH₂CH₂Cl)₂
2    : n-3,  R=CH₂OCON(CH₂CH₂Cl)₂ prednimustine, WB4291 (1-[bis(2-chloroethyl)amino]-3-methylnaphthalene), daunomycin and vincristine.

Preferred cytotoxic agents to be employed herein will depend upon the particularly neoplastic disease to be treated as follows.

|  | Target (absorbs LDL) | Cytotoxic Agent to be Employed |
|---|---|---|
| (1) | acute myeloid leukemia | compounds 25, 1, 2 and the other preferred compounds listed above |
| (2) | human monocytic (FAB-M5) and myelomonocytic (FAB-M4) leukemias and chronic myeloid leukemia in blast crisis | |
| (3) | epidermoid cervical cancer | |
| (4) | endometrial adenocarcinoma | |
| (5) | gastric carcinoma | |
| (6) | parotid adenoma | |
| (7) | brain tumors including medulloblastoma, oligodendroglioma, and malignant meningioma | |
| (8) | squamous and small cell lung tumors | |
| (9) | glioma | |
| (10) | G2 hepatoma | |
| (11) | choriocarcinoma | |
| (12) | metastatic tumors | |
| (13) | lymphoma | |
| (14) | bladder cancer | |
| (15) | breast carcinoma | |

The dosages and formulations for the MTP inhibitor delipidating agent will be as disclosed in the various patents and applications discussed above.

The dosages and formulations for the delipidating agent and cytotoxic agent to be employed, where applicable, will be as set out in the latest edition of the Physicians' Desk Reference.

Dosages for the LDL-drug conjugate are as follows: from about 10 to about 1000 mg/day, preferably from about 50 to about 250 mg/day, when the patient is at least 90% delipidated, in single or divided doses (2 to 4 times/day). The reconstituted LDL portion will comprise about 50% of the conjugate.

The LDL-drug conjugate may be formulated for intravenous administration employing conventional pharmaceutical practices.

What is claimed is:

1. A method for treating a cancer having a high LDL requirement, which comprises administering to a mammalian species in need of treatment a therapeutically effective amount of a delipidating drug to substantially reduce LDL blood level to less than 20% of normal LDL blood level.

2. The method as defined in claim 1 wherein the LDL blood level is less than 10% of normal LDL blood level.

3. The method as defined in claim 1 wherein the LDL blood level is reduced to substantially zero.

4. The method as defined in claim 1 wherein the delipidating compound is an MTP inhibitor alone or in combination with another type of cholesterol lowering drug.

5. The method as defined in claim 4 wherein the MTP inhibitor has the structure

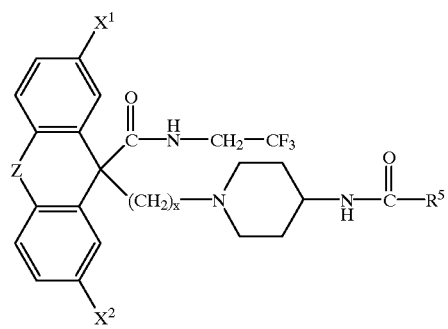

including the piperidine N-oxide thereof or a pharmaceutically acceptable salt thereof, wherein Z is a bond, O or S;

$X^1$ and $X^2$ are independently selected from H or halo;

x is an integer from 2 to 6;

$R^5$ is heteroaryl, aryl, heterocycloalkyl or cycloalkyl, each $R^5$ group being optionally substituted with 1, 2, 3 or 4 substituents which may be the same or different.

6. The method as defined in claim 5 where in the MTP inhibitor Z is a bond.

7. The method as defined in claim 5 where the MTP inhibitor is a piperidine N-oxide.

8. The method as defined in claim 5 where in the MTP inhibitor $(CH_2)_x$ is optionally substituted with 1, 2 or 3 substituents which are the same or different and are alkyl or halo.

9. The method as defined in claim 5 where in the MTP inhibitor $R^5$ is substituted with 1, 2, 3 or 4 substituents which may be the same or different and are halogen, monocyclic heteroaryl, bicyclic heteroaryl, heteroarylalkyl, cycloheteroalkyl, alkyl, alkoxy, cycloalkyl, aryl, aryloxy, substituted aryl, arylalkyloxy, heteroaryloxy, amino, alkylamino, alkyl(aryl)amino, heteroarylamino, arylamino, alkylthio, arylthio, arylthioalkyl, heteroarylthio, arylsulfinyl or acyl.

10. The method as defined in claim 9 wherein the MTP inhibitor the $R^5$ includes a substituent attached to a carbon in the position adjacent to the carbon linked to

11. The method as defined in claim 9 wherein the MTP inhibitor $R^5$ is substituted with 1, 2, 3 or 4 of one or more of the following

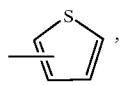,

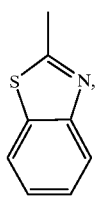,

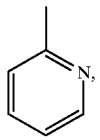,

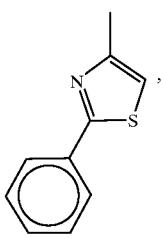,

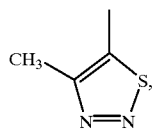,

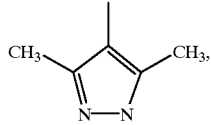,

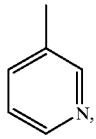,

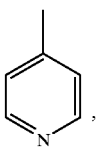,

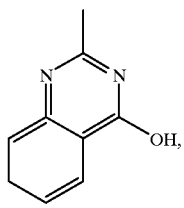

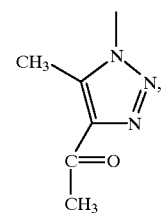

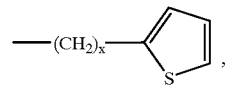, where x is 1 to 5

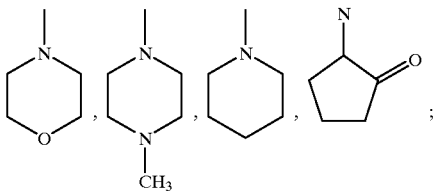;

alkyl, phenyl, phenyl substituted with halo, alkyl, $CF_3O$, alkoxy,

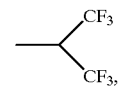

$CF_3$, or phenyl;

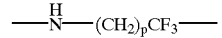

where p is 1 to 5, —$N(CH_3)C_6H_5$; —S—$(CH_2)_p CF_3$ where p is 1 to 5,

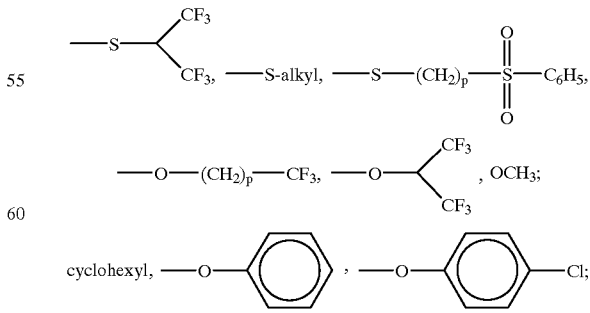

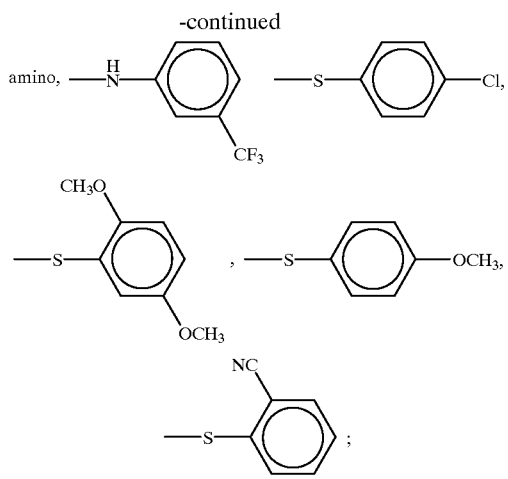

alkanoyl, alkoxycarbonyl, aroyl, heteroarylaminocarbonyl, arylalkyloxycarbonyl,

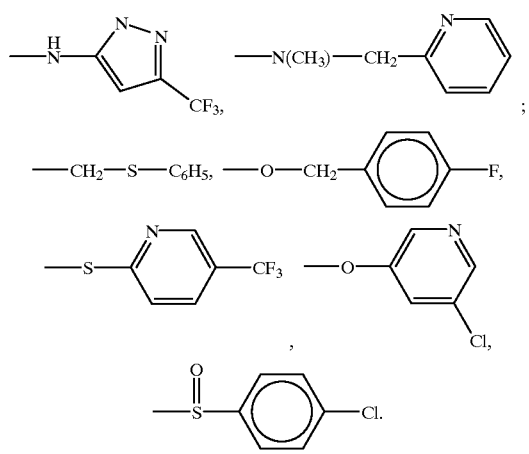

12. The method as defined in claim 11 where in the MTP inhibitor $R^5$ is phenyl substituted with haloalkylphenyl or heteroaryl.

13. The method as defined in claim 12 where in the MTP inhibitor $R^5$ is

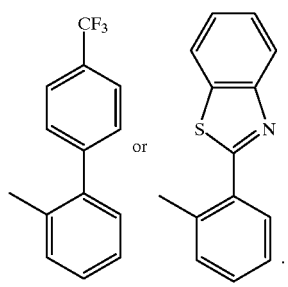

14. The method as defined in claim 11 where in the MTP inhibitor is

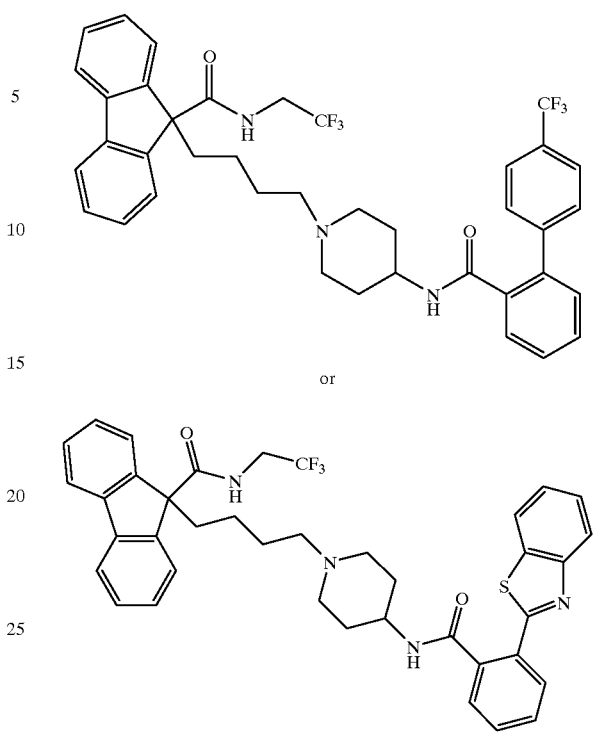

15. The method as defined in claim 4 wherein the MTP inhibitor has the structure

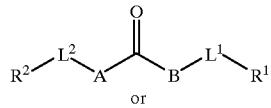   I

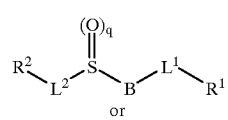   IA

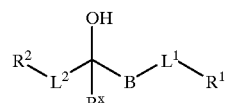   IB including pharmaceutically acceptable salts thereof, N-oxides thereof, wherein q is 0, 1 or 2;

A is
 (1) a bond;
 (2) —O—; or

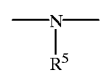

where $R^5$ is H or lower alkyl, or $R^5$ together with $R^2$ forms a carbocyclic or heterocyclic ring system containing 4 to 8 members in the ring;

B is a fluorenyl-type group of the structure

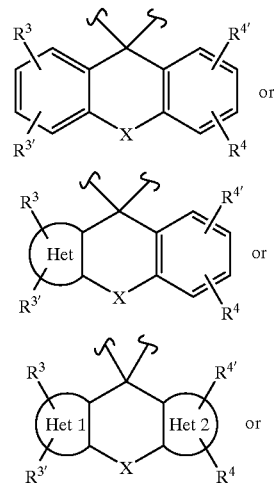

B is an indenyl-type group of the structure

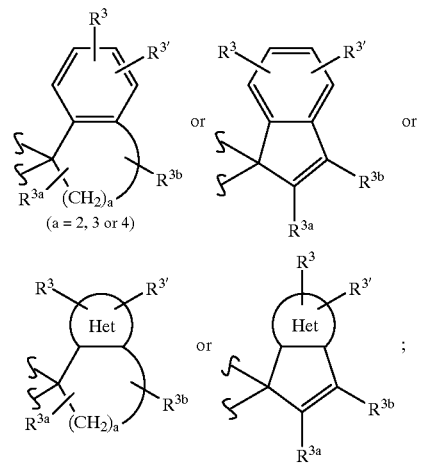

$R^x$ is H, alkyl or aryl;

$R^1$ is alkyl, alkenyl, alkynyl, alkoxyl, (alkyl or aryl)$_3$Si (where each alkyl or aryl group is independent), cycloalkyl, cycloalkenyl, substituted alkylamino, substituted arylalkylamino, aryl, arylalkyl, arylamino, aryloxy, heteroaryl, heteroarylamino, heteroaryloxy, arylsulfonylamino, heteroarylsulfonylamino, arylthio, arylsulfinyl, arylsulfonyl, alkylthio, alkylsulfinyl, alkylsulfonyl, heteroarylthio, heteroarylsulfinyl, heteroarylsulfonyl, —PO($R^{13}$) ($R^{14}$), (where $R^{13}$ and $R^{14}$ are independently alkyl, aryl, alkoxy, aryloxy, heteroaryl, heteroarylalkyl, heteroaryloxy, heteroarylalkoxy, cycloheteroalkyl, cycloheteroalkylalkyl, cycloheteroalkoxy, or cycloheteroalkylalkoxy); aminocarbonyl (where the amino may optionally be substituted with one or two aryl, alkyl or heteroaryl groups); cyano, 1,1-(alkoxyl or aryloxy)$_2$alkyl (where the two aryl or alkyl substituents can be independently defined, or linked to one another to form a ring connected to $L^1$ (or $L^2$ in the case of $R^2$) at the 2-position); 1,3-dioxane or 1,3-dioxolane connected to $L^1$ (or $L^2$ in the case of $R^2$) at the 4-position; the $R^1$ group may optionally be substituted with 1, 2, 3 or 4 substituents, which can be any of the $R^3$ or $R^1$ groups or alkylcarbonylamino, cycloalkylcarbonylamino, arylcarbonylamino, heteroarylcarbonylamino, alkoxycarbonylamino, aryloxycarbonylamino, heteroaryloxylcarbonylamino, uriedo (where the uriedo nitrogens may optionally be substituted with alkyl, aryl or heteroaryl), heterocyclylcarbonylamino (where the heterocycle is connected to the carbonyl group via a nitrogen or carbon atom), alkylsulfonylamino, arylsulfonylamino, heteroarylsulfonylamino,

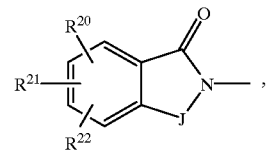

where J is: $CHR^{23}$,

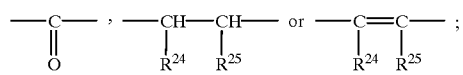

$R^{23}$, $R^{24}$ and $R^{25}$ are independently hydrogen, alkyl, alkenyl, alkynyl, aryl, arylalkyl, heteroaryl, heteroarylalkyl, cycloalkyl, or cycloalkylalkyl;

$R^{20}$, $R^{21}$, $R^{22}$ are independently hydrogen, halo, alkyl, alkenyl, alkoxy, aryloxy, aryl, arylalkyl, alkylmercapto, arylmercapto, cycloalkyl, cycloalkyl-alkyl, heteroaryl, heteroarylalkyl, hydroxy or haloalkyl; and these substituents may either be directly attached to $R^1$, or attached via an alkylene at an open position;

$R^2$ is independently any of the groups set out for $R^1$, H, polyhaloalkyl, or cycloheteroalkyl, and may be optionally substituted with one to four of any of the groups defined for $R^3$ or substituents defined for $R^1$;

$L^1$ is a linking group containing from 1 to 10 carbons in a linear chain including alkylene, alkenylene or alkynylene, which may contain, within the linking chain any of the following: one or two alkenes, one or two alkynes, an oxygen, an amino group, an oxo group, and may be substituted with one to five alkyl or halo groups;

$L^2$ may be the same or different from $L^1$ and may independently be any of the $L^1$ groups set out above or a singe bond;

$R^3$, $R^{3'}$, $R^4$ and $R^{4'}$ may be the same or different and are independently selected from H, halogen, $CF_3$, haloalkyl, hydroxy, alkoxy, alkyl, aryl, alkenyl, alkenyloxy, alkynyl, alkynyloxy, alkanoyl, nitro, amino, thiol, alkylthio, alkylsulfinyl, alkylsulfonyl, carboxy, alkoxycarbonyl, aminocarbonyl, alkylcarbonyloxy, alkylcarbonylamino, cycloheteroalkyl, cycloheteroalkylalkyl, cyano, Ar—, Ar-alkyl, ArO, Ar-amino, Ar-thio, Ar-sulfinyl, Ar-sulfonyl, Ar-carbonyl, Ar-carbonyloxy or Ar-carbonylamino, wherein Ar is aryl or heteroaryl and Ar may optionally include 1, 2 or 3 additional rings fused to Ar;

$R^{3a}$ and $R^{3b}$ are the same or different and are independently any of the $R^3$ groups except hydroxy, nitro, amino or thio;

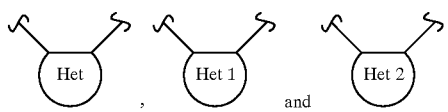

are the same or different and independently represent a 5 or 6 membered heteroaryl ring which contains 1, 2, 3 or 4 heteroatoms in the ring which are independently N, S or O; and including N-oxides;

X is a bond, or is one of the following groups:

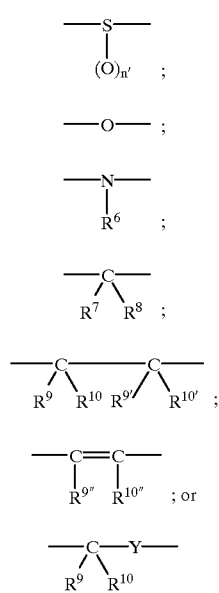

wherein
Y is O, N—$R^6$ or S;
n' is 0, 1 or 2;
$R^6$ is H, lower alkyl, aryl, —C(O)—$R^{11}$ or —C(O)—O—$R^{11}$;
$R^7$ and $R^8$ are the same or different and are independently H, alkyl, aryl, halogen, —O—$R^{12}$, or
$R^7$ and $R^8$ together can be oxygen to form a ketone;
$R^9$, $R^{10}$, $R^{9'}$ and $R^{10'}$ are the same or different and are independently H, lower alkyl, aryl or —O—$R^{11}$;
$R^{9''}$ and $R^{10''}$ are the same or different and are independently H, lower alkyl, aryl, halogen or —O—$R^{11}$;
$R^{11}$ is alky or aryl;
$R^{12}$ is H, alkyl or aryl;
with the following provisos for compound of the structure

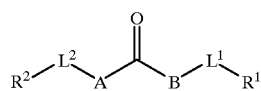

(a) when $R^1$ is unsubstituted alkyl or unsubstituted arylalkyl, $L^1$ cannot contain amino;
(b) when $R^1$ is alkyl, $L^1$ cannot contain amino and oxo in adjacent positions (to form an amido group);
(c) when $R^2L^2A$— is $H_2N$—, $R^1L^1$ cannot contain amino;
(d) when $R^1$ is cyano, $L^1$ must have more than 2 carbons;
(e) $R^1L^1$ must contain at least 3 carbons;

with respect to compounds of formulas I, IA and IB, where $R^1$ is cycloheteroalkyl, $R^1$ is exclusive of 1-piperidinyl, 1-pyrrolidinyl, 1-azetidinyl or 1-(2-oxo-pyrrolidinyl);

with respect to the sulfur containing compounds and alcohols, $R^2L^2$ cannot have an O or N atom directly attached to $S=(O)_q$ or $CR^x(OH)$, and for IA, $R^2L^2$ cannot be H.

16. The method as defined in claim 15 wherein the MTP inhibitor has the structure

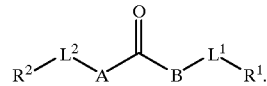

17. The method as defined in claim 16 wherein A is a bond.

18. The method as defined in claim 16 wherein A is —O—.

19. The method as defined in claim 16 wherein A is

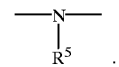

20. The method as defined in claim 16 wherein B is a fluorenyl-type group.

21. The method as defined in claim 16 having the formula

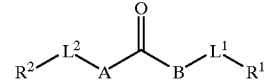

wherein B is

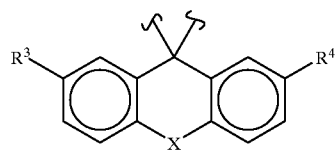

A is NH;
X is a bond, oxygen or sulfur;
$R^3$ and $R^4$ are the same or different and are H or F;
$R^1$ is aryl, phenyl, heteroaryl, imidazolyl, pyridyl, cyclohexyl, $PO(R^{13})$ ($R^{14}$), heteroarylthio, benzthiazole-2-thio, imidazole-2-thio, alkyl, alkenyl or 1,3-dioxan-2-yl, wherein each of the above is optionally substituted;
$R^2$ is alkyl, polyfluoroalkyl, alkenyl, aryl, phenyl, heteroaryl, imidazolyl or pyridyl, wherein each of the above is optionally substituted;
$L^1$ is a chain containing 1 to 5 atoms in a linear chain;
$L^2$ is a bond or lower alkylene.

22. The method as defined in claim 1 wherein the cancer to be treated is a hematologic tumor.

23. The method as defined in claim 1 wherein the cancer to be treated is a solid tumor or a metastatic tumor.

24. The method as defined in claim 1 wherein the cancer treated is acute myeloid leukemia.

25. A method for treating a cancer having a high LDL requirement, which comprises administering to a mammalian species in need of treating a therapeutically effective amount of one or more delipidating drugs which substantially reduces LDL blood level to less than 20% of normal LDL blood level and a cytotoxic agent.

26. A method for treating cancers having a high LDL requirement, which comprises administering to a mammalian species in need of treatment an LDL lowering amount of a delipidating compound to substantially remove native LDL, and then administering a cytotoxic agent in reconstituted LDL to said mammalian species.

27. The method as defined in claim 26 wherein the delipidating compound is an MTP inhibitor alone or in combination with another cholesterol lowering drug.

28. The method as defined in claim 26 wherein the cancer to be treated is a hematologic tumor.

29. The method as defined in claim 26 wherein the cancer to be treated is acute myeloid leukemia.

* * * * *

UNITED STATES PATENT AND TRADEMARK OFFICE
CERTIFICATE OF CORRECTION

PATENT NO.   : 5,990,110
DATED        : Nov. 23, 1999
INVENTOR(S)  : Raymond A. Firestone It is certified that error appears in the above-identified patent and that said Letters Patent is hereby corrected as shown below:

In Column 33, Line 23, after "arylalkyloxycarbonyl," please insert -- $-CH_2-S-C_6H_5$, --.

In Column 34, Line 60, please insert -- (3) -- before the structure.

Signed and Sealed this

Sixteenth Day of January, 2001

Attest:

Q. TODD DICKINSON

*Attesting Officer*     *Commissioner of Patents and Trademarks*